United States Patent [19]
Saito et al.

[11] Patent Number: 4,992,368
[45] Date of Patent: Feb. 12, 1991

[54] NOVEL PROCESS FOR PRODUCING OXETANOCIN G

[75] Inventors: Seiichi Saito, Kashiwa; Shigeru Hasegawa; Masayuki Kitagawa, both of Urawa; Nobuyoshi Shimada, Tokyo; Noriyuki Yamashita, Yono, all of Japan

[73] Assignee: Nippon Kayaku Kabushiki Kaisha, Tokyo, Japan

[21] Appl. No.: 508,910

[22] Filed: Apr. 12, 1990

[30] Foreign Application Priority Data

Apr. 20, 1989 [JP] Japan ..................... 1-98907
Aug. 25, 1989 [JP] Japan ..................... 1-217216

[51] Int. Cl.$^5$ .................. C07D 473/00; C12P 19/40
[52] U.S. Cl. ........................ 435/88; 544/265; 544/276
[58] Field of Search ............... 435/88; 544/276, 265

[56] References Cited

U.S. PATENT DOCUMENTS 4,845,215 7/1989 Shimada et al. ............... 544/265
4,892,876 1/1990 Hoshino et al. ............... 514/265

OTHER PUBLICATIONS

The Journal of Antibiotics, vol. XL, No. 12, pp. 1788–1790 1987.
Derwent Abs 89-279633/39 XRAMC89-123739 (EP-334250)9-89 Saito et al.
Derwent Abs 88-331503/47 XRAM C88-14653-3(EP-291917)11-88 Shimada et al.
Jour. Antibiot (1986) 39, 11, 1623-25 Biotech Abs 87-01947 Shimada et al.

Primary Examiner—Herbert J. Lilling
Attorney, Agent, or Firm—Henry C. Nields

[57] ABSTRACT

The present invention provides a novel process for producing oxetanocin G by hydrolysis of alkoxylated 2-amino-oxetanocin A thereby to convert

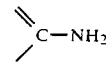

at the 6-position thereof into >C=O.
Oxetanocin G is expectedly useful as an antiviral agent.

7 Claims, No Drawings

NOVEL PROCESS FOR PRODUCING OXETANOCIN G

BACKGROUND OF THE INVENTION

Field of the invention

The present invention relates to a novel process for producing oxetanocin G. The present invention also relates to intermediates for synthesis of oxetanocin G.

Description of the Prior Art

Oxetanocin G is a compound which is expected to be useful as an antiviral agent, etc. and is disclosed in EP-A-0291917, together with a process for production thereof. This known process comprises either performing microbiological conversion with respect to the steps of starting from oxetanocin A to obtain oxetanocin X and then performing chemical synthesis up to 2-amino-oxetanocin A, or applying chemical synthesis to all of the steps up to 2-amino-oxetanocin A and finally performing enzymatic conversion to obtain oxetanocin G.

However, this known process involves problems that in the case of the microbiological conversion, large amount of microbial cells are required, its reaction time is prolonged, etc. On the other hand, the overall chemical synthesis encounters a problem in yield so that such a process is not suited for industrial production.

Therefore, the present inventors have made extensive investigations on a process for producing oxetanocin G suitable for mass production and as a result, have accomplished the present invention.

SUMMARY OF THE INVENTION

Accordingly, an object of the present invention is to provide a process for producing oxetanocin G (hereinafter merely referred to as OXT-G) which is suited for industrial production.

The present invention provides a process for producing OXT-G which comprises hydrogenolizing an alkoxylated 2-amino-oxetanocin A (referred to as alkoxy-2-amino-OXT-A) represented by formula (I) to obtain 2amino-oxetanocin A (referred to as 2-amino-OXT-A) and then converting

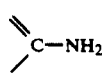

at the 6-position thereof into >C=O.

DETAILED DESCRIPTION OF THE INVENTION

The present invention relates to a process for producing OXT-G (including salts thereof) which comprises hydrogenolizing alkoxy-2-amino-OXT-A (including salts thereof) represented by general formula (I):

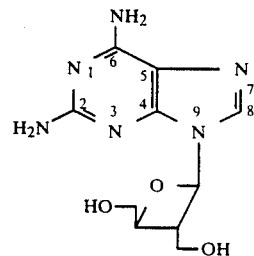

(wherein R₁ represents a lower alkyl group) to remove the alkoxy group and obtain 2-amino-OXT-A (including salts thereof) represented by the following formula:

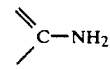

and then converting

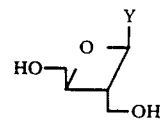

at the 6-position thereof into 22 C=O.

The present invention also relates to oxetanocin derivatives represented by general formula (II):

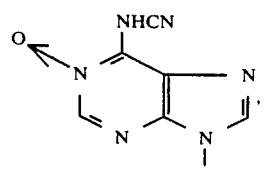

wherein Y represents:

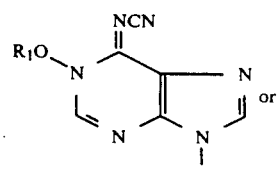

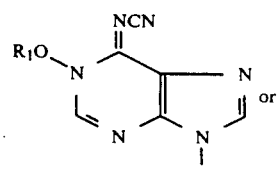 or

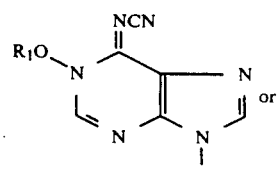

-continued

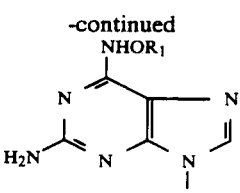

(wherein R₁ represents a lower alkyl group)] which are used as intermediates for synthesis of OXT-G.

The hydrogenolysis of the alkoxy-2-amino-OXT-A represented by general formula (I) can be carried out by catalytic reduction in a solvent.

Any solvent is usable so long as it does not inhibit the reaction; however, a polar solvent, for example, a polar organic solvent, water or a solvent mixture of water and the polar organic solvent is generally used. As the polar organic solvent, it is preferred to use a lower alcohol such as methanol, ethanol, etc.

As the catalyst, there may be used catalysts used for ordinary catalytic reduction, for example, platinum type catalysts, palladium type catalysts, nickel type catalysts, cobalt type catalysts, etc. In general, palladium type catalysts such as Pd-C, etc. are used.

The reaction is carried out generally in the presence of hydrogen at about 0° C. to about 150° C. under normal pressure to under pressure, e.g., at about 1 to about 20 atoms.

The reaction time can vary depending upon kind of catalyst or reaction temperature and is not limited to a certain period but about 1 to about 10 hours are sufficient for the reaction.

For forming the slats of 2-amino-OXT-A, the following procedure applies.

2-Amino-OXT-A is suspended in water and an acid is added to the suspension to dissolve 2-amino-OXT-A. Then, a suitable solvent is added to the solution to crystallize the salts. Any acid can be used for forming the salts as long as it is a pharmacologically acceptable acid. Preferred examples are hydrochloric acid, sulfuric acid, phosphoric acid, etc.

Examples of the lower alkyl group in general formula (I) or (II) include an alkyl group having 1 to 6 carbon atoms, preferably 1 to 4 carbon atoms such as methyl, ethyl, propyl and butyl, etc.

In order to convert

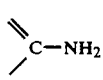

at the 6-position to >C═O, either the chemical method or the enzymatic method may be used but the enzymatic method is generally used. As the enzyme, adenosine deaminase, adenylic acid deaminase or the like may be used. These enzymes may be those commercially available, for example, EC 3.5.4.4 manufactured by Sigma Co. as adenosine deaminase and, as adenylic acid deaminase, 5'-adenylic acid deaminase (Catalogue No. A-1907) manufactured also by Sigma Co., or DEAMIZYME ® (trademark) manufactured by Amano Pharmaceutical Co., Ltd., etc. These enzymes may not be pure but the culture of microorganism and treated matters thereof or products collected from animal tissue may also be used so long as they contain these enzymes.

For producing OXT-G from 2-amino-OXT-A using these enzymes, 2-amino-OXT-A and these enzymes are reacted with each other in an aqueous solvent, for example, water or a solvent mixture of water and a polar solvent (a lower alcohol or the like) at pH of about 5 to about 9, preferably about 6 to about 8, at a temperature of about 10° C. to about 70° C., preferably about 20° C. to about 50° C., more preferably about 20° C. to about 40° C. As the solvent, it is preferred to use a buffer solution, preferably, phosphate buffer solution for pH stabilization. In general, there may be used about 0.05 to about 2.5 M, preferably about 0.1 to about 2.0 M of phosphate buffer (pH of about 5 to about 8).

It is difficult to a set a general range for the quantity of enzyme to be used since the quantity varies depending upon purity of enzyme, etc. but it is preferred that for example, A-1907 (adenylic acid deaminase) manufactured by Sigma Co. be used in a quantity of about 10,000 to about 50,000 units per 1 mole of 2-amino-OXT-A. The optimum quantity to be used is approximately 20,000 to 30,000 units.

In the case of EC 3.5.4.4 (adenosine deaminase) manufactured by Sigma Co., it is preferred to use 2,000 to 200,000 units per 1 mole of 2-amino-OXT-A. The optimum quantity used is approximately 25,000 to 50,000 units. In this case, the enzymatic method can be carried out according to the process described in EP-A-0291917.

To isolate the product from the reaction solution, a convertional manner may be applicable. For the isolation, a method for utilizing difference in solubility in water or an organic solvent, adsorption-desorption method using activated charcoal, adsorbing resin or ion exchange resin, and the like can be used in a suitable combination.

For example, colorless crystalline OXT-G can be obtained by reacting 2-amino-OXT-A with the enzyme, passing the reaction solution through a column packed with porous resin to adsorb the product thereto, then either eluting the product with water, concentrating and evaporating off to dryness or eluting with a solvent mixture of water-lower alcohol (methanol, ethanol or the like), concentrating the desired fraction and evaporating off to dryness. If necessary and desired, the obtained OXT-G can be further purified using Sephadex ® or the like.

The alkoxy-2-amino-OXT-A represented by general formula (I) which is used as the raw compound in the present invention can be produced by the following steps. (I) Process for producing alkoxy-2-amino-OXT-A;

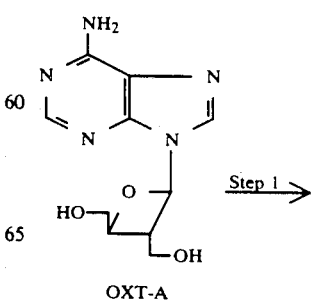

OXT-A

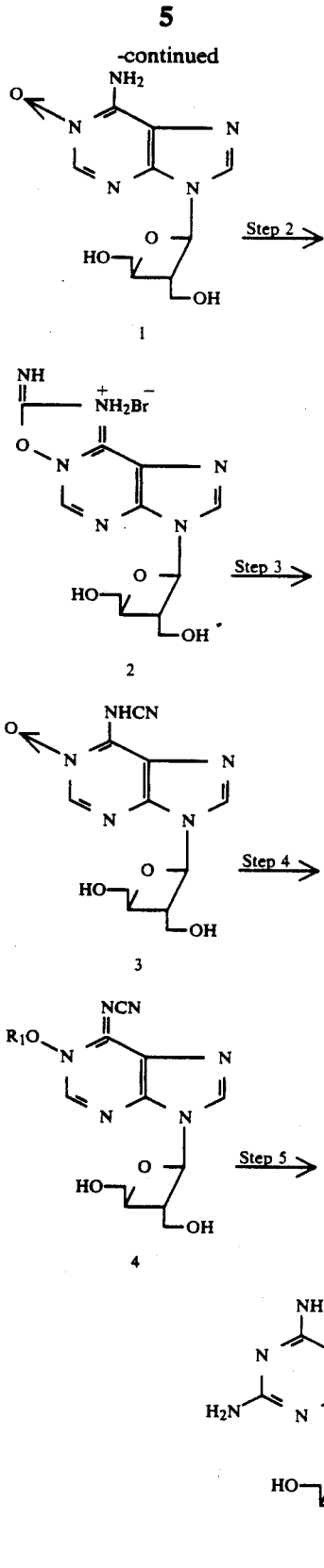

amino-OXT-A (Compound 1). Hereafter, the respective steps are described in more detail.

Step 1

Oxetanocin A (OXT-A) is N-oxidated with an appropriate oxidizing agent. Examples of the oxidizing agent include m-chloroperbenzoic acid, peracetic acid, hydrogen peroxide, etc. The oxidizing agent may be used in about 0.5 to about 5 equimolar amounts based on OXT-A. The reaction may be carried out at a temperature in the range of from about 0° C. to about 100° C.

The reaction described above is carried out generally in an appropriate solvent. As the reaction solvent, there may be used a polar organic solvent such as acetic acid, acetone, dioxane, methanol, ethanol and the like which may include water. The reaction may also be carried out in the dual layer solvent system consisting of a nonpolar organic solvent such as chloroform, ethyl acetate, etc. and water. N-oxide of OXT-A (Compound 1) can be purified by removing the reagents by extraction with ethyl acetate followed by column chromatography.

Step 2

In this step, a cyanogen halide is reacted with Compound 1 to form the oxadizole ring. Examples of the cyanogen halide include cyanogen bromide, cyanogen iodide, etc. The cyanogen halide may be used in approximately 0.5 to 10 equimolar amounts. The reaction temperature is generally between about 0° C. and about 100° C.

Step 3

In this step, the hydrogen chloride is removed from the hydrogen chloride salt of Compound 2 with ammonia-saturated alcohol. As the solvent, it is preferred to use an organic solvent such as methanol, ethanol, etc. The reaction is carried out at a temperature in a range of from about 0° C. to about 60° C.

Step 4

The Compound 3 is alkylated in a suitable solvent at a temperature of about 0° C. to the boiling point of a solvent (about 150° C.) in the presence of a base. The reaction is carried out generally under normal pressure but may be under pressure. As the solvent, a polar organic solvent such as N,N-dimethylformamide, acetone, pyridine, etc. are preferred. Examples of the base include mono, di or tri lower alkyl amines such as triethylamine, diisopropylethylamine, etc. As the alkylating agent, an alkyl halogenide such as methyl iodide, ethyl iodide, etc. can be used.

Step 5

In this step, the base moiety of Compound 4 is subjected to ring-opening with a base, rearrangement and then ring closure by heating in a polar solvent. As the base, there may be used an alkali metal hydroxide, for example, sodium hydroxide, potassium hydroxide, and an alkaline earth metal hydroxide, etc. In addition thereto, an organic base such as triethylamine or the like may also be used. As the polar solvent, an alcoholic solvent such as aqueous methanol, aqueous ethanol, etc. are preferred. The heating is effected in a range of from about 30° C. to about 150° C. but generally in a range of from about 50° C. to about 80° C.

That is, after oxetanocin A (OXT-A) is converted into the N-oxide, cyano group is substituted on the amino group via the oxadiazole ring. The resulting N-oxide compound is alkylated and then subjected to ring-opening, rearrangement and ring closure to obtain alkoxy-2-

In the steps 1 through 5, the product may not be isolated at each step, unless inconvenience is involved. Alternatively, these steps may be performed continuously several steps in one batch. For example, the steps 2 to 4 may also be carried out in one batch, using a polar solvent such as dimethylformamide, etc.

EXAMPLE 1

(1) Synthesis of 2-amino-OXT-A

To a solution of 53.8 g of alkoxy-2-amino-OXT-A (Compound 5) ($R_1$=ethyl) in 50% aqueous ethanol, 16 g of 10% Pd-C was added to hydrogenolize for 4 hours in the presence of hydrogen at 95° to 105° C. under 12 to 14 atms. After the catalyst was filtered off, the solvent was concentrated. The residue was crystallized from 500 ml of hot water to give 34.4 g of crude 2-amino-OXT-A. By washing the crude product with 150 ml of hot water, 32.7 g of 2-amino-OXT-A.½H$_2$O was obtained. 2Amino-OXT-A.½H$_2$O: FE-MS /mz; 266 (M)+

UV: λH$_2$O/max nm; 256, 278

NMR (200 MHz, DMSO-d$_6$, TMS) ppm; 8.30 (1H, s, 8-H). 6.80 (2H, bs, NH$_2$), 6.23 (1H, d, J=5.84Hz, 1'-H), 5.88(2H, bs, NH$_2$), 5.39(1H, t, OH), 5.0(1H, t, OH), 4.48(1H, m, 3'-H), 3.50–3.80 (3H, m)

Element analysis: Calcd: C: 43.94%, H: 5.49%, N: 30.90%. Found: C: 43.63%, H: 5.30%, N: 30.53%.

(2) Synthesis of 2-amino-OXT-A salt (hydrochloride)

In 33 ml of water was suspended 5.0 g of 2-amino-OXT-A-½H$_2$O and, 3.42 ml of hydrochloric acid (hydrogen chloride: 20%) was added to the suspension to dissolve the salt and then 33 ml of ethanol was added to the solution. The mixture was allowed to settle at 5° C. for 20 hours. The precipitated crystals were filtered and washed with a small quantity of 50% aqueous ethanol and then with a small quantity of ethanol. After drying under reduced pressure, 29.3 g of 2-amino-OXT-A.HCl was obtained. 2Amino-OXT-A.HCl: molecular formula: $C_{10}H_{14}N_6O_3HCl$ Elemental analysis: Calcd: C: 40.04%, H: 5.02%, N: 28.48%, Cl: 10.31%. Found: C: 39.68%, H: 5.00%, N: 27.76%, Cl: 11.71%.

NMR (200 MHz, D$_2$O) ppm; 8.30(1H, s, 8-H), 6.29(1H, d, J=4.8Hz, 1'-H), 4.65(1H, m, 3'-H). 3.60–3.95(5H, m)

(3) Synthesis-1 of OXT-G

After 2.0 g of 2-amino-OXT-A was dissolved in 300 ml of 1/10 M phosphate buffer (pH 6.5), 200 units of 5'-adenylic acid deaminase (manufactured by Sigma Co., A-1907) were added to the solution followed by stirring at 37° C. for 50 hours. After the reaction solution was passed through a column packed with MCI® GEL CHP 20 (300 ml) and the reaction products were adsorbed onto it, the products were eluted by water. Fractions showing an Rf value of about 0.42 in silica gel TLC [developing solvent: n-butanol-acetic acid-water (4:1:2)] were collected and concentrated to dryness under reduced pressure to give 1.8 g of OXT-G as colorless crystals (yield, 90%).

FE-MS: 268 (M+H)+

UV : λpH 6.0/max (log ε) 253.5 nm (4.09)

NMR (400 MHz, D$_2$O) ε ppm; 3.69–3.87(5H, m), 4.66–4.69(1H, m), 6.29(1H, d), 8.17(1H, s)

(4) Synthesis-2 of OXT-G

After 2.0 g of 2-amino-OXT-A was dissolved in 300 ml of 1/10 M phosphate buffer (pH 6.5), 8.0 g of 5'-adenylic acid deaminase (manufactured by Amano Pharmaceutical Co., Ltd. DEAMIZYME®) was added to the solution followed by stirring at 37° C. for 70 hours. After insoluble matters of the reaction solution were removed by filtration, the filtrate was passed through a column packed with 50 ml of activated charcoal powders (manufactured by Wako Pure Chemical Industry K.K., for chromatography). After washing with water, elution was performed with 50% aqueous methanol. By concentrating the desired fraction to dryness, crude OXT-G was obtained. The crude powders were dissolved in 50 ml of water and the OXT-G in the solution was adsorbed onto MCI® GEL CHP 20 (300 ml) followed by elution with water. The desired fraction was concentrated and evaporated to dryness under reduced pressure to give 1.5 g of OXT-G as colorless crystals (yield, 75%).

The alkoxy-2-amino-OXT-A used as a starting material was synthesized as follows.

Synthesis of alkoxy-2-amino-OXT-A (Compound 5) form OXT-A

(a) Synthesis of Compound 1

After 150 g of OXT-A was dissolved in a mixture of 2.2 liters of water and 1 liter of methanol, 0.75 liter of a solution of 139 g of m-chloroperbenzoic acid in methanol was added to the solution. Under light shielding, the mixture was stirred at room temperature for 18 hours and 0.15 liter of a solution of 28 g of m-chloroperbenzoic acid in methanol was further added to the reaction mixture. Stirring were performed for further 5 hours.

After insoluble matters were filtered off, the filtrate was concentrated to 2.0 liters and the concentrate was extracted twice with 1.5 liters of ethyl acetate. After the aqueous phase was concentrated to 1.5 liter, 0.5 liter of water was added to the residue. The mixture was passed through a column packed with 2.0 liters of MCI® GEL CHP 20. The passing liquid and washing liquid (8.2 liters) were collected and concentrated to dryness to give 146.4 g of Compound 1 (yield, 91.7%).

Compound 1 : FAB-MS m/z; 268 (M+H)

NMR (60 MHz, D$_2$O) pm; 8.87(1H, s), 8.73(1H, s), 6.71(1H, d), 4.70(1H, m), 3.99–4.30(5H, m), 4.66(1H, m, 3'-H)

(b) Synthesis of Compound 2Π

After 129.3 g of Compound 1 was dissolved in 5.7 liters of methanol, 0.45 liters of a solution of 55.5 g of cyanogen bromide in methanol was added to the solution. The mixture was stirred at room temperature for 2 hours.

Compound 2 was precipitated but for further precipitating the compound, 3.0 liters of ethyl acetate were added to the mixture followed by stirring for 20 minutes. The precipitated crystals were filtered and washed with ethyl acetate. After drying under reduced pressure, 146.48 g (yield, 81.1%) of Compound 2 was obtained as colorless crystals. The method liquid was concentrated and crystallized from 1 liter of methanol and 1 liter of ethyl acetate. By performing the same procedure, 13.26 g (yield, 7.3%) of Compound 2 was obtained as colorless crystals.

Compound 2 : FD-MS m/z; 294 (M+H-Br)+,

IR (KRr); 1720 cm$^{-1}$ (C=NH)

NMR (200 MHz, DMSO-d$_6$ TMS) ppm; 10.70(1H, bs, NH), 10.13(1H, s, 8-H), 9.35(1H, s, 2-H), 6.61(1H, d, J=4.84Hz, 1'-H), 4.70(1H, m), 2.50(3H, m)

UV λH$_2$O/max nm: 223, 283

(c) Synthesis of Compound 3

After 159.6 g of Compound 2 was suspended in 6 liters of methanol, 1.6 l of ammonia-saturated methanol was added to the suspension (the compound 2 was dissolved). The solution was stirred at room temperature for 1.5 hour. The reaction solution was concentrated to the half volume an the precipitated colorless crystals were filtered. After washing with a small quantity of methanol, the crystals were dried under reduced pressure to give 118.1 g (yield, 94.6%) of Compound 3.

Compound 3 : FD-MS m/z; 293 (M+H)+,
IR (KBr); 2170 cm$^{-1}$(N—C≡N), 1220 cm$^{-1}$(N—O)
UV λH$_2$O/max nm; 247, 293
NMR (200 MHz, D$_2$O) ppm: 8.55 (1H, s, 8-H), 8.42(1H, s, 2-H), 6.46(1H, d, J=5.49Hz, 1'-H) 4.70 (1H, m, 3'-H), 3.72–4.00 (5H, m)

(d) Synthesis of Compound 4

After 109.06 of Compound 3 was suspended in 1.1 liter of N,N-dimethylformamide, 85.2 ml of triethylamine and 60.6 ml of ethyl iodide were added to the suspension. The mixture was stirred at room temperature for 2 hours. The solvent was concentrated under reduced pressure. After the residue was dissolved in 1.4 liter of hot water, the solution was allowed to stand at room temperature and the resulting gel-like precipitates were filtered to give 118.47 g (yield, 99.2%) of crude Compound 4.

Compound 4 : FD-MS m/z; 320 (M)+
IR (KBr); 2180 cm$^{-1}$ (C N)
UV λMeOH/max mm: 220, 285
NMR (200 MHz, CD$_3$OD, TMS) ppm: 8.84(1H, s, 8-H) 8.68(1H, s, 2-H), 6.52(1H, d, J=5.78 Hz, 1'-H), 4.69(1H, m, 3'-H), 4.43(2H, q, J=7.01 Hz, —C$\underline{H}$$_2$—CH$_3$), 3.65-3.97 (3H, m), 1.44(3H, 5, J=7.01 Hz, —CH$_2$—C$\underline{H}$$_3$)

(e) Synthesis of Compound 5

After 107.6 g of Compound 4 was suspended in 2.3 liters of water, 86 ml of 5 N sodium hydroxide was added to the suspension. The mixture was stirred at room temperature for 2.5 hours. A pH of the reaction solution was adjusted to 7.3 with Dowex ® 50 (H+) and the resin was filtered off. To the filtrate was added 2.3 liters of ethanol. The mixture was heated to reflux for 30 minutes and the resulting reaction solution was used in the following step as it was.

Compound 5 : FD-MS m/z; 310 (M)+
UV λH$_2$O/max nm; 280
NMR (200 MHz, DMSO-d$_6$, TMS) ppm; 9.70(1H, bs, NH). 8.07(1H, s, 8-H), 6.60(2H, bs, NH$_2$), 6.11 (1H, d, J=5.95 Hz, 1'-H), 5.20(1H, t, OH), 4.96(1H, t, OH), 4.46(1H, m, 3'-H), 3.98(2H, q, J=7.04 Hz, OC$\underline{H}$$_2$—CH$_3$), 3.40–3.70 (5H, m), 1.05(3H, t, J=7.04 Hz, —OCH$_2$—C$\underline{H}$$_3$)

What is claimed is:

1. A process for producing oxetanocin G represented by the following formula:

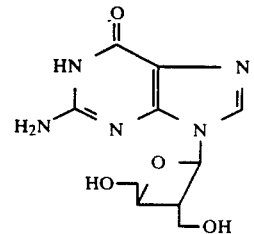

which comprises (b 1) hydrogenolizing an alkoxylated 2-amino-oxetanocin A represented by general formula (I) below:

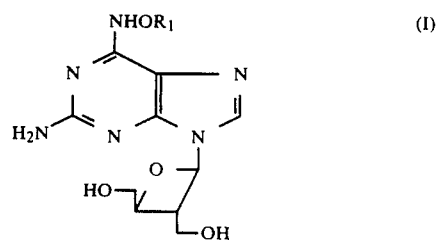

(wherein R$_1$ represents a lower alkyl group) to convert into 2-amino-oxetanocin A represented by formula:

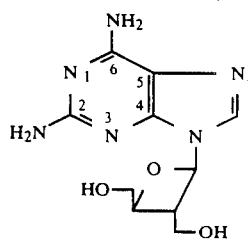

and (2) then converting

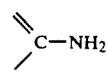

at the 6-position thereof into 22 C═O.

2. A process according to claim 1, wherein said conversion of

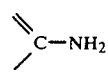

at the 6-position thereof into >C═O is effected using adenosine deaminase or adenylic acid deaminase.

3. A process according to claim 1, wherein said hydrogenolysis of the alkoxylated 2-amino-oxetanocin A is carried out by catalytic reduction in a polar solvent.

4. A process according to claim 1, wherein said hydrogenolysis is carried out at a temperature of from 0° C. to 150° C.

5. A process according to claim 2, wherein said conversion is carried out in an aqueous solvent at a pH value of from about 5 to about 9 at a reaction temperature of from about 10° C. to about 70° C.

6. A process according to claim 5, wherein said conversion is carried out at the pH value of about 6 to about 8 at a reaction temperature of from about 20° C. to about 50° C.

7. A process according to claim 1, wherein said alkoxylated-2-amino oxetanocin A represented by the formula (I)

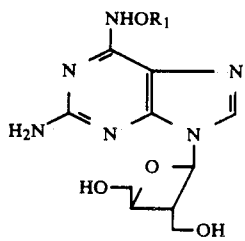

is prepared by (1) alkylating a cyanated N-oxide oxetanocin A represented by the following formula:

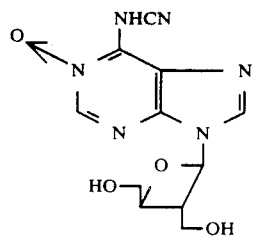

to obtain a cyano-N-alkoxyoxetanocin A represented by the following formula:

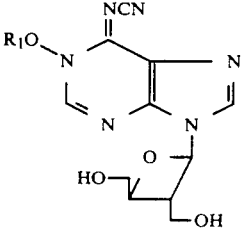

(wherein $R_1$ represents a lower alkyl group), (2) then treating said compound with an alkali, (3) neutralizing and (4) heating.

* * * * *